(12) United States Patent
Harsch

(10) Patent No.: US 9,216,113 B2
(45) Date of Patent: Dec. 22, 2015

(54) HEARING PROTECTION EARPIECE

(75) Inventor: Samuel Harsch, Ballaigues (CH)

(73) Assignee: Sonova AG, Stäfa (CH)

( * ) Notice: Subject to any disclaimer, the term of this patent is extended or adjusted under 35 U.S.C. 154(b) by 78 days.

(21) Appl. No.: 14/360,067

(22) PCT Filed: Nov. 23, 2011

(86) PCT No.: PCT/EP2011/070865
§ 371 (c)(1),
(2), (4) Date: May 22, 2014

(87) PCT Pub. No.: WO2013/075744
PCT Pub. Date: May 30, 2013

(65) Prior Publication Data
US 2014/0321660 A1    Oct. 30, 2014

(51) Int. Cl.
*A61F 11/08* (2006.01)
*H04R 1/10* (2006.01)
*H04R 31/00* (2006.01)
*A61F 11/12* (2006.01)
*A61F 11/14* (2006.01)

(52) U.S. Cl.
CPC .............. *A61F 11/08* (2013.01); *H04R 1/1083* (2013.01); *H04R 31/00* (2013.01); *A61F 11/12* (2013.01); *A61F 2011/085* (2013.01); *A61F 2011/145* (2013.01); *A61F 2240/002* (2013.01); *Y10T 29/49002* (2015.01); *Y10T 29/4957* (2015.01)

(58) Field of Classification Search
CPC .............. H04R 2499/11; H04R 1/1041; H04R 1/1016; H04R 1/1058; H04R 1/1091; H04R 1/02
USPC .......................................................... 360/72
See application file for complete search history.

(56) References Cited

U.S. PATENT DOCUMENTS

| | | | |
|---|---|---|---|
| 4,677,678 A | 6/1987 | McCutchen | |
| 5,742,689 A | 4/1998 | Tucker et al. | |
| 6,002,775 A | 12/1999 | Wood et al. | |
| 6,533,062 B1 | 3/2003 | Widmer et al. | |
| 6,766,878 B2 | 7/2004 | Widmer et al. | |
| 8,213,629 B2* | 7/2012 | Goldstein | H04R 1/1041 381/107 |
| 8,311,228 B2* | 11/2012 | Goldstein | A61B 5/121 381/56 |
| 8,331,593 B2* | 12/2012 | Slemming | H04R 25/656 381/318 |
| 8,917,894 B2* | 12/2014 | Goldstein | H04R 3/002 381/23.1 |
| 2003/0133583 A1 | 7/2003 | Widmer et al. | |
| 2010/0119077 A1 | 5/2010 | Platz et al. | |
| 2011/0130786 A1 | 6/2011 | Clayton et al. | |

FOREIGN PATENT DOCUMENTS

| | | |
|---|---|---|
| EP | 1 355 508 A2 | 10/2003 |
| EP | 1 674 061 A1 | 6/2006 |
| EP | 1 322 268 B1 | 1/2009 |
| WO | 02/071794 A1 | 9/2002 |
| WO | 2007/073818 A1 | 7/2007 |
| WO | 2007/082579 A2 | 7/2007 |
| WO | 2007/123788 A2 | 11/2007 |
| WO | 2009/050306 A2 | 4/2009 |
| WO | 2009/153221 A2 | 12/2009 |
| WO | 2010/048157 A1 | 4/2010 |
| WO | 2010/092307 A1 | 8/2010 |
| WO | 2010/133701 A2 | 11/2010 |
| WO | 2011/033136 A2 | 3/2011 |

* cited by examiner

*Primary Examiner* — Mark Blouin
(74) *Attorney, Agent, or Firm* — Roberts Mlotkowski Safran & Cole, PC; David S. Safran

(57) ABSTRACT

A hearing protection earpiece having a shell shaped according to conform to the user's concha and ear canal and having an open hollow lateral portion to be inserted into the user's concha and a medial portion to be inserted into at least an outer portion of the user's ear canal, wherein the medial portion of the shell is axially adjacent to the lateral portion of the shell, wherein the lateral portion of the shell forms part of an open portion of the earpiece and the medial portion of the shell forms part of a closed portion of the earpiece, wherein the earpiece provides for a mechanical sound attenuation of at least 10 dB averaged over the audible frequency range, and wherein the lateral portion of the shell has a wall thickness of not more than 3 mm and is shaped to cover at least half of the concha area.

24 Claims, 3 Drawing Sheets

HEARING PROTECTION EARPIECE

BACKGROUND OF THE INVENTION

1. Field of the Invention

The invention relates to a hearing protection earpiece comprising a customized shell.

2. Description of Related Art

Customized earpieces are earpieces comprising a hard shell which has an outer surface individually shaped according to the measured inner shape of the user's outer ear and ear canal. Such shape measurement can be carried out, for example, by direct laser scanning of the user's ear or by forming an impression which then is laser-scanned. The customized hard shell may be produced by an additive process, such as layer-by-layer laser sintering of a powder material. Customized earpieces of this type are described, for example, in International Patent Application Publication WO 02/071794 A1, and U.S. Pat. Nos. 6,766,878 B2 and 6,533, 062 B1.

In general, hearing protection devices may be passive or active, i.e., dynamic. Passive hearing protection earpieces typically comprise a passive acoustic filter which allows for some frequency adjustment of the sound attenuation. Dynamic hearing protection earpieces comprise a microphone for capturing audio signals from ambient sound and a loudspeaker for emitting sound into the ear canal; in addition, an audio signal processing unit for processing the audio signals captured by the microphone and for supplying processed audio signals to the loudspeaker is provided, either as part of the earpiece or as a separate body-worn unit. With active hearing protection devices level-dependent attenuation of sound is achieved, so that protection from high noise levels can be realized while at low noise levels perception of useful sound can be perceived without the need to remove the hearing protection device. Examples of active hearing protection earpieces are found, for example, in European Patent Application EP 1 674 061 A1, and International Patent Application Publications WO 2007/082579 A2, WO 2009/050306 A2 and WO 2010/133701 A2.

One problem encountered with hearing protection devices is that the ability of the user to localize a sound source is significantly deteriorated when wearing the hearing protection device. This applies in particular to the localization in elevation and to front-back discrimination. However, in particular for military or police applications or in certain industrial working applications, an accurate localization of sound sources is of major importance to the user of the hearing protection device. In critical situations, this may result in the problem that the user decides to not wear the hearing protection device.

U.S. Pat. No. 4,677,678 relates to a hearing protection earmuff comprising an outer microphone, an audio signal processing unit including an automatic gain control (AGC) circuit and a loudspeaker. Since such arrangement acoustically by-passes the pinna, localization information is partially lost or significantly modified.

International Patent Application Publication WO 2011/033136 A2 relates to a dynamic hearing protection device which is completely worn in the ear canal, whereby localization information may be preserved to a high extent.

EP 1 322 268 B1 relates to a dynamic hearing protection earplug comprising both an outer microphone for capturing ambient sound and an inner microphone oriented towards the ear canal for capturing the user's voice. The earplug is designed to fill part of the concha and may be combined with an audio communication device for enabling wireless communication with other persons.

Dynamic hearing protection earpieces of the full concha type having a customized shell filling the concha are available under the product designation "Serenity" from Phonak Communications AG, Murten, Switzerland.

U.S. Pat. Nos. 5,742,689 and 6,002,775, and International Patent Application Publications WO 2010/092307 A1, WO 2007/123788 A2 and WO 2010/048157 A1 describe various methods of combining multiple audio sources into two stereo channels supplied to headphones/earphones by using head-related transfer functions (HRTF), with the positions of the sources being known.

U.S. Patent Application Publication 2011/0130786 A1 relates to a device for treating headache, which is designed as an intra-aural device comprising a rigid shell which is provided with a scalloped indenture which is open towards ambience.

SUMMARY OF THE INVENTION

It is an object of the invention to provide for a hearing protection earpiece allowing for good sound localization, especially with regard to elevation and front-back discrimination.

According to the invention, this object is achieved by a hearing protection earpiece as described herein.

The invention is beneficial in that, by providing an earpiece with a hollow lateral portion covering at least half of the concha area, preferably, substantially the entire concha area, and having a wall thickness of the shell of not more than 3 mm, preferably not more than 2 mm, with the medial portion of the shell forming part of a closed portion of the earpiece, good retention of the earpiece in the user's ear is achieved while, as a result of the relatively high preservation of the original shape of the pinna, only relatively little localization information is lost, so that good sound source localization can be achieved. In particular, due to the relatively small disturbance of the original shape of the pinna ensured by the thin wall thickness of the portion of the shell covering the concha area, the individual HRTF, which is crucial for sound localization, in particular for localization in elevation and for front-back discrimination, is essentially preserved (by contrast, the individual HRTF may be significantly lost when wearing earpieces of the full-concha-type having a shell which completely fills the concha).

Hereinafter, examples of the invention will be described in detail with reference to the accompanying drawings.

DETAILED DESCRIPTION OF THE INVENTION

Figure 1:
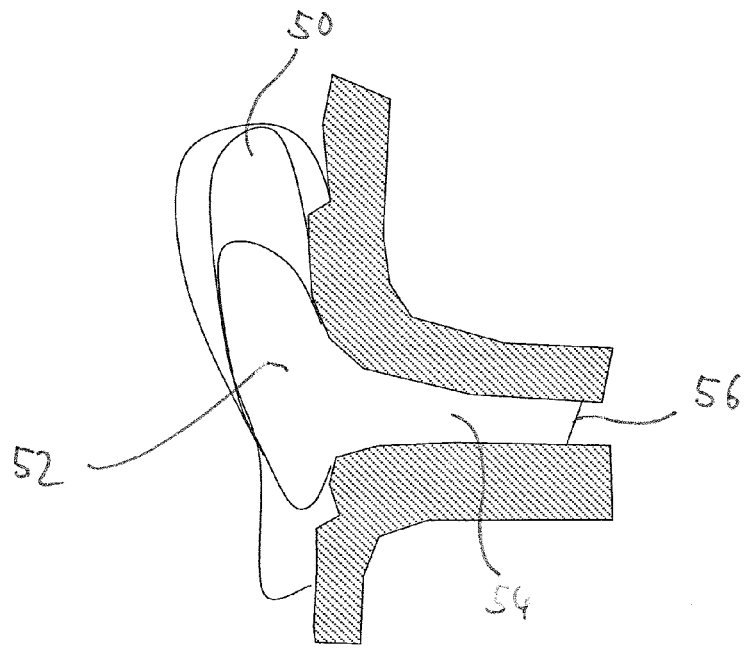
FIG. 1 is a schematic sectional view of the outer ear of a person.

FIG. 1 shows a schematic representation of the outer ear comprising the pinna 50, the concha 52, the ear canal 54 and the eardrum 56.

Figure 2:
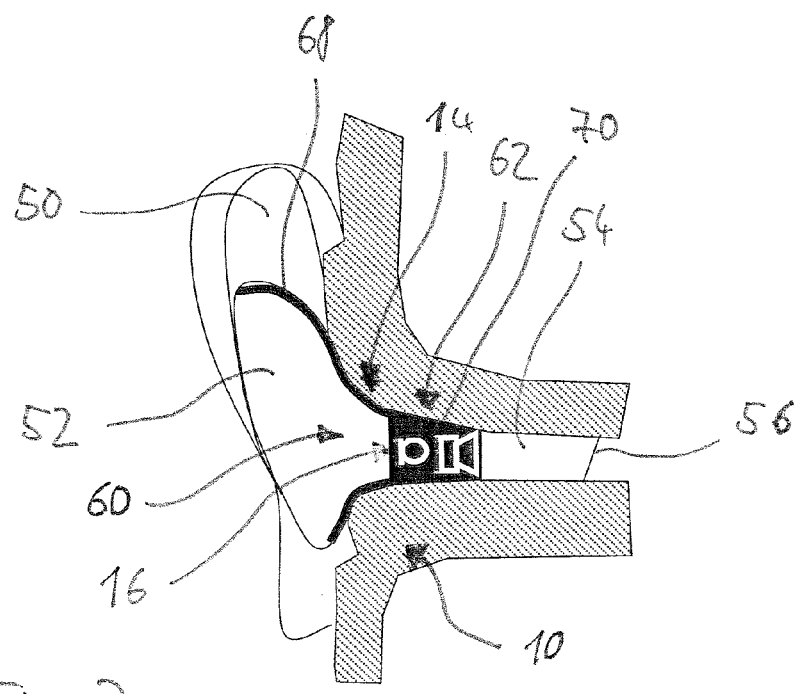
FIG. 2 is a schematic cross-sectional view of a first embodiment of a hearing protection earpiece according to the invention when inserted into the ear.

In FIG. 2, a first example of a hearing protection earpiece 10 according to the invention is shown inserted into the outer ear. The earpiece 10 comprises an open lateral portion 60 and a closed medial portion 62 ("lateral" means away from the eardrum 56 and "medial" means towards the eardrum 56) and also comprises a shell 14 and an electronics assembly 16. The shell 14 comprises an open hollow lateral portion 68 to be inserted into the concha 52 and a medial portion 70 which is axially adjacent to the lateral portion 68 and which is for being inserted into at least an outer portion of the ear canal 54. The lateral shell portion 68 is shaped to cover at least half of—and preferably the entire—concha area so as to conform with the concha 52 and has a wall thickness of not more than 3 mm, preferably not more than 2 mm.

The medial shell portion 70 comprises a receptacle or channel extending axially into or through the medial shell portion 70, with the electronics assembly 16 being inserted in such a manner that the medial shell portion 70 and the inserted electronics assembly 16 together form the closed portion 62 of the earpiece 10 in order to provide for a mechanical sound attenuation of the earpiece of at least 10 dB averaged over the audible frequency range. The electronics assembly 16 may be inserted into the medial shell portion in a replaceable or fixed manner. The lateral shell portion 68 primarily serves to keep the earpiece 10 in place in the user's ear, so that the earpiece 10 can provide for a reliable hearing protection function with regard to ambient noise, but in addition also contributes to the mechanical sound attenuation of the earpiece.

Typically, the earpiece 10 will provide for a (passive) acoustic attenuation of about 25 dB for medium frequencies (the attenuation typically is higher for higher frequencies, for example, increasing from about 20 dB at low frequencies to about 30 dB for high frequencies). Preferably, the lateral shell portion 68 forms a continuous, imperforate wall, i.e., it does not have substantial openings or holes extending into or through the wall, thus having essentially smooth surfaces on both sides. The reason is that with such a continuous imperforate wall, a higher contribution of the lateral shell portion 68 to the overall mechanical attenuation provided by the earpiece is achieved.

The shell 14 is a customized shell, i.e., a hard or soft, but a firm shell having an outer surface individually shaped according to the inner shape of the user's outer ear and ear canal, which may be measured, for example, by direct laser scanning or by forming an impression which then is laser-scanned is preferred. The customized shell may be produced by an additive process, such as layer-by-layer laser sintering of a powder material. Customized shells are described, for example, in U.S. Patent Application Publication 2003/0133583 A1. Preferably, the shell 14 is made of nylon.

Figure 3:
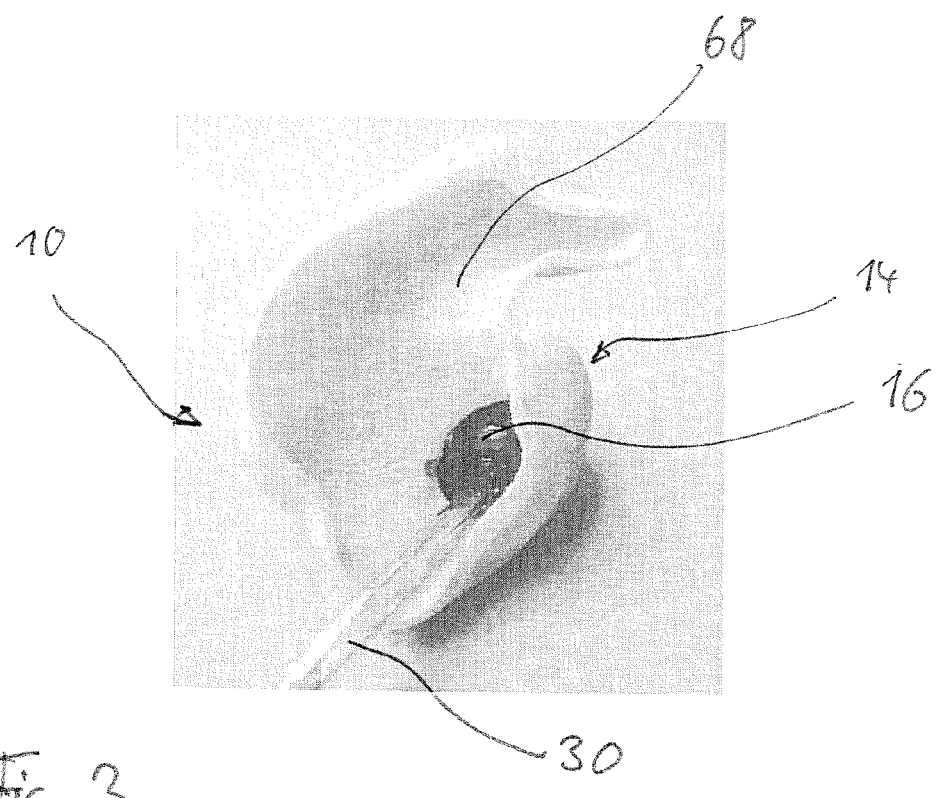
FIG. 3 is a perspective view of an example of an earpiece according to the invention.

FIG. 3 is a perspective view of an example of an earpiece 10 of the type shown in FIG. 2.

Figure 5:
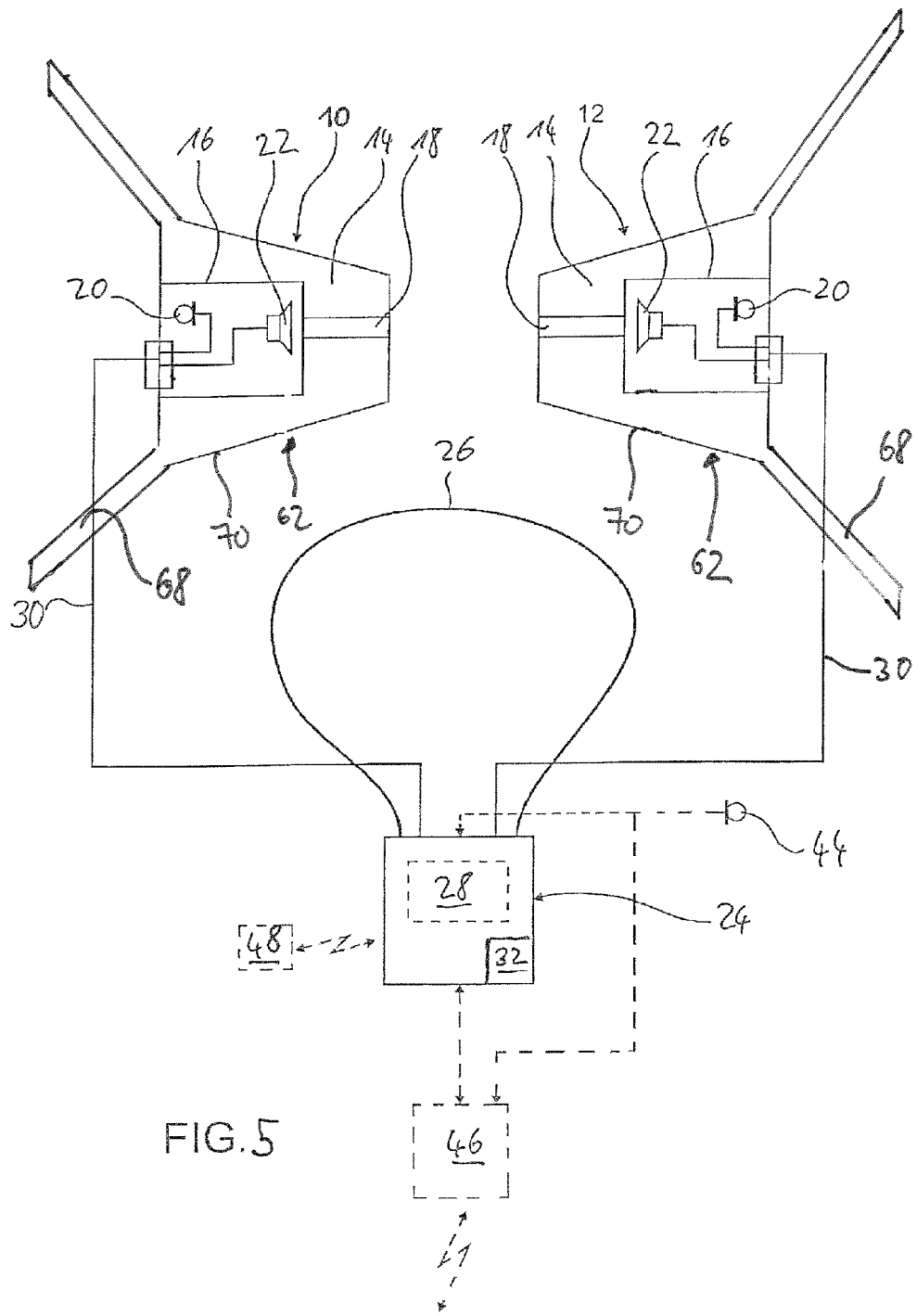
FIG. 5 is a schematic view of an example of a dynamic hearing protection system using two earpieces of the type shown in FIGS. 2 and 3.

FIG. 5 shows an example of a dynamic hearing protection system which also may include a wireless communication capability and which utilizes two earpieces 10, 12 of the type of the earpiece 10 shown in FIGS. 2 and 3. Each earpiece 10, 12 is provided with an electronics assembly 16 for adjusting the frequency dependency of the sound attenuation and the degree of sound attenuation provided by each earpiece 10, 12. In the example of FIG. 5, the electronics assembly 16 is inserted into a corresponding receptacle formed in the medial portion 70 of the shell 14 and is locked there by corresponding locking means (not shown) in a releasable manner so that the shell 14 can be easily replaced, for example, if damaged or for cleaning purposes.

The medial shell portion 70 is provided with a sound channel 18 by which the electronics assembly 16 is acoustically connected to the ear canal 54.

The electronics assembly 16 comprises an outwardly oriented microphone 20 for capturing audio signals from ambient sound and an inwardly oriented loudspeaker 22 for delivering sound waves into to the user's ear canal 54 via the sound channel 18.

The system also comprises an external unit 24 which is to be worn at the user's body below the user's neck, for example, by a loop 26 around the user's neck, and which comprises an audio signal processing unit 28 for processing the audio signals captured by the microphones 20, in order to supply the loudspeakers 22 with audio signals to be reproduced to the user's hearing. To this end, the electronic units 16 are connected to the external unit 24 via cable connections 30. Alternatively, the connection may be wireless, such as via an inductive link (not shown). The external unit 24 may be provided with a user interface 32 comprising, for example, a button or a wheel for enabling the user to manually control the function of the audio signal processing unit 28. The cable connections 30 serve to electrically connect the respective microphone 20 to the input of the audio signal processing unit 28 and the respective loudspeaker 22 to the output of the audio signal processing unit 28.

The audio signal processing unit 28 typically is designed to reduce the gain applied to the audio signals above a given threshold signal input level in order to provide for a dynamic sound attenuation with level compression and/or level limitation. For example, the gain applied by the audio signal processing unit 28 may be constant below such threshold signal input level and may be monotonously decreasing with increasing signal input level when the signal input level is above the threshold signal input level. For example, a gain model may be chosen such that, above the threshold signal input level, the output sound pressure level in the ear canal 54 is constant, irrespective of the signal input level. An example of such gain model is described in International Patent Application Publication WO 2007/082579 A2 and corresponding U.S. Patent Application Publication 2010/0119077.

Preferably, the closed portion 62 of the earpiece 10 has an axial length of 4 to 12 mm.

The closed portion 62 of the earpiece 10 serves to provide for the desired sound attenuation function, whereas the open portion 60 of the earpiece, although providing for some sound attenuation, primarily serves to produce good retention of the earpiece 10 within the concha 52. Due to the open nature of the open portion 60 achieved by the small wall thickness of not more than 3 mm, significant loss of localization information is avoided since the original shape of the pinna 56 is essentially preserved.

The microphones 20 may be located at the outer end of the closed earpiece portion 62 at the entrance of the ear canal 54, but also could be placed deeper in the ear canal. Thereby, the individual HRTF of the user can be essentially preserved in the captured and reproduced sound.

As the wavelength of the elevation information and front/back information of the sound source is in relation with the physical dimensions of the pinna 50, the system, i.e., the microphones 20, the audio signal processing unit 28 and the loudspeakers 22, should have a bandwidth of at least 14 kHz.

In addition to the components discussed so far, the hearing protection system could be provided with a communication function, wherein at least one additional microphone would be provided for capturing the user's voice. Such additional microphone may be a boom microphone attached to one of the earplugs (as indicated in FIG. 5 at 44 in dashed lines), or each of the earplugs may be provided with an additional microphone facing towards the ear canal, in order to pick up the user's voice by using a blind source separation algorithm (see, for example, WO 2007/073818 A1).

An example of a system comprising a boom microphone is described in WO 2007/082579 A2 and corresponding U.S. Patent Application Publication 2010/0119077. In both cases, the audio signal processing unit would be connected to a communication device, for example, an FM transceiver (as indicated in FIG. 5 at 46), in order to send the audio signals corresponding to the captured voice of the user to another person or to receive audio signals to be presented via the loudspeakers 22 from an external source, such as another person.

According to an alternative embodiment, the user interface 32 may be implemented as a remote control (indicated in FIG. 5 at 48) rather than being provided as part of the central unit 24.

Figure 4:
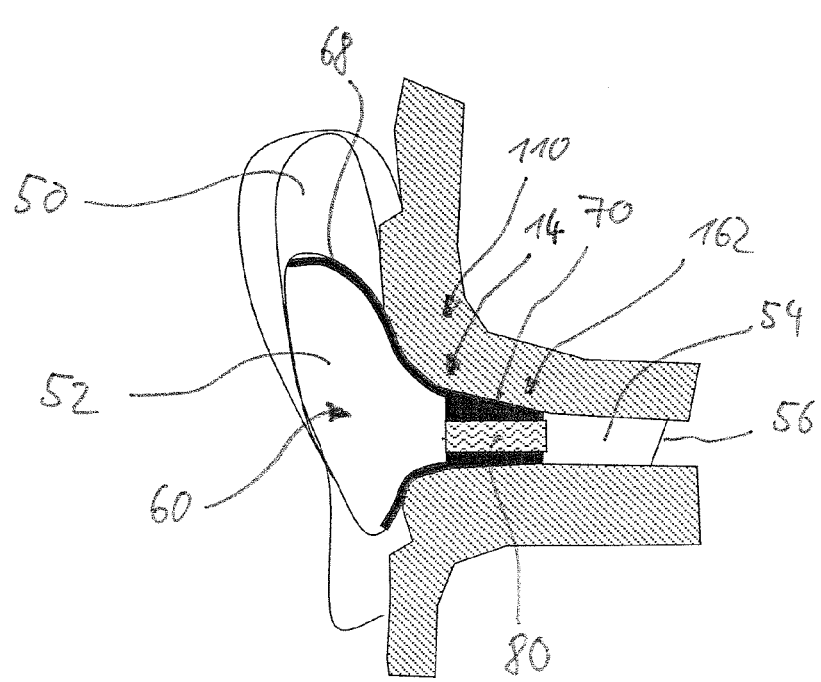
FIG. 4 is a view like FIG. 2, wherein an alternative embodiment of an earpiece according to the invention is shown.

According to an alternative embodiment, the earpiece may be designed as a passive hearing protection device, wherein the earpiece includes a passive acoustic filter rather than an active electronics assembly 16. An example of such passive earpiece 110 is schematically shown in FIG. 4, wherein the medial shell portion 70 is designed to receive a passive acoustic filter 80 which extends axially into or through the medial shell portion 70. Preferably, the acoustic filter 80 is replaceably inserted into a receptacle extending into the medial shell portion 70 or into a channel extending axially through the medial shell portion 70. When designed as a passive hearing protection device, the closed portion 162 of the earpiece 10 may have a shorter axial length, e.g., down to 1 mm or less, than in the case of a dynamic hearing protection device. The passive acoustic filter 80 may be a non-linear impulse noise filter, i.e., a filter providing for increased sound attenuation at higher level sound impulses compared to lower level continuous sound. Such filters may be used as shot filters for military or hunting applications.

The passive acoustic filter can be a porous element, a resistive mesh, a membrane or a combination of those elements.

What is claimed is:

1. A hearing protection earpiece, comprising:
a shell having a shape matched to the shape of a particular user's concha and ear canal and having an open hollow lateral portion for insertion into the user's concha in shape conform therewith and a medial portion for insertion into at least an outer portion of the user's ear canal,
wherein the medial portion of the shell is axially adjacent to the lateral portion of the shell,
wherein the lateral portion of the shell forms part of an open portion of the earpiece,
wherein the medial portion of the shell forms part of a closed portion of the earpiece,
wherein the earpiece is adapted to provide mechanical sound attenuation of at least 10 dB averaged over the audible frequency range, and
wherein the lateral portion of the shell has a wall thickness of at most 3 mm and is shaped to cover at least half of the concha area.

2. The earpiece of claim 1, wherein the closed portion of the earpiece comprises a passive acoustic filter extending axially into or through the medial portion of the shell.

3. The earpiece of claim 2, wherein the passive acoustic filter is a non-linear impulse noise filter providing sound attenuation of higher level sound impulses that is increased as compared to lower level continuous sound.

4. The earpiece of claim 2, wherein the passive acoustic filter is replaceably located in a channel extending axially into or through the medial portion of the shell.

5. The earpiece of claim 2, wherein the passive acoustic filter is one of a porous element, a resistive mesh, a membrane and a combination thereof.

6. The earpiece of claim 1, wherein the closed portion of the earpiece comprises a microphone for capturing audio signals from ambient sound and a loudspeaker for emitting sound into the ear canal.

7. The earpiece of claim 6, wherein the closed portion of the earpiece comprises means for electrically connecting the microphone to the input of an audio signal processing unit and means for electrically connecting the loudspeaker to an output of an audio signal processing unit.

8. The earpiece of claim 7, wherein the audio signal processing unit forms part of an external unit to be worn at the user's body below the user's neck.

9. The earpiece of claim 7, wherein the microphone, the loudspeaker and the audio signal processing unit are designed to provide for an audio bandwidth of at least 14 kHz.

10. The earpiece of claim 7, wherein the audio signal processing unit is adapted to reduce gain applied to the input audio signals above a given threshold signal input level to provide for dynamic sound attenuation with at least one level compression and level limitation.

11. The earpiece of claim 10, wherein the gain applied by the audio signal processing unit is constant below the threshold signal input level and is monotonously reduced with increasing signal input level above the threshold signal input level.

12. The earpiece of claim 6, wherein the microphone and the loudspeaker form part of an assembly which is replaceably inserted into an opening extending axially into or through the medial portion of the shell.

13. The earpiece of claim 6, wherein the closed portion of the earpiece has an axial length of from 1 to 12 mm.

14. The earpiece of claim 1, wherein the shell is made of nylon.

15. The earpiece of claim 1, wherein the lateral portion (68) of the shell (14) is shaped to cover the entire concha area.

16. The earpiece of claim 1, wherein the lateral portion of the shell has an imperforated wall.

17. A hearing protection system, comprising:
two hearing protection earpieces, each of which comprises:
a shell having a shape matched to the shape of a particular user's concha and ear canal and having an open hollow lateral portion for insertion into the user's concha in shape conform therewith and a medial portion for insertion into at least an outer portion of the user's ear canal,
wherein the medial portion of the shell is axially adjacent to the lateral portion of the shell,
wherein the lateral portion of the shell forms part of an open portion of the earpiece,
wherein the medial portion of the shell forms part of a closed portion of the earpiece,
wherein the earpiece is adapted to provide mechanical sound attenuation of at least 10 dB averaged over the audible frequency range, and
wherein the lateral portion of the shell has a wall thickness of at most 3 mm and is shaped to cover at least half of the concha area,
wherein the closed portion of the earpiece comprises a microphone for capturing audio signals from ambient sound and a loudspeaker for emitting sound into the ear canal, and wherein the closed portion of the earpiece comprises means for electrically connecting the microphone to the input of an audio signal processing unit and means for electrically connecting the loudspeaker to an output of an audio signal processing unit; and an external unit to be worn at the user's body below the user's neck and containing said audio signal processing unit.

18. The system of claim 17, further comprising means for connecting the audio signal processing unit to a wireless communication device.

19. A method of manufacturing the hearing protection earpiece that provides mechanical sound attenuation of at least 10 dB averaged over the audible frequency range, comprising the steps of:

measuring the shape of the concha and ear canal of a particular user's ear;

forming a shell for an earpiece in accordance with the measured shape of the concha and ear canal of the particular user's ear by a layer by layer build-up process in a manner providing an open hollow lateral portion for insertion into the user's concha as part of an open portion of the earpiece and forming an medial portion for insertion into at least an outer portion of the user's ear canal that is adjacent to the lateral portion of the shell, the lateral portion of the shell being formed with a wall thickness of at most 3 mm and a shape sufficient to cover at least half of the concha area of the of particular user's ear, and inserting means for providing mechanical sound attenuation of at least 10 dB averaged over the audible frequency range into said medial portion to form a closed portion of the earpiece.

20. The method of claim 19, wherein the layer by layer build-up process is a selective laser is one of a sintering (SLS) process and a digital light processing (DLP) process.

21. The method of claim 19, wherein the means for providing mechanical sound attenuation inserted into the medial portion of the shell comprises a passive acoustic filter.

22. The method of claim 19, wherein the means for providing mechanical sound attenuation inserted into the medial portion of the shell comprises a microphone for capturing audio signals from ambient sound, a loudspeaker for emitting sound into the ear canal, means for electrically connecting the microphone to the input of an audio signal processing unit and means for electrically connecting the loudspeaker to the output of the audio signal processing unit.

23. The method of claim 19, wherein the shape of the concha and ear canal of the particular user's ear is measured by taking an impression of the user's ear and optically measuring the shape of the impression.

24. The method of claim 23, wherein the shape of the concha and ear canal of the particular user's ear is measured by laser scanning of the user's ear.

* * * * *